(12) United States Patent
Sun et al.

(10) Patent No.: US 12,326,413 B2
(45) Date of Patent: Jun. 10, 2025

(54) POTENTIOMETRIC BIOSENSOR AND DETECTION METHOD

(71) Applicant: LEADWAY (HK) LIMITED, Hong Kong (CN)

(72) Inventors: Yu Long Sun, Zhejiang (CN); Xin Liang Xiang, Zhejiang (CN); Yan Cheng, Zhejiang (CN); Li Zhang, Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 644 days.

(21) Appl. No.: 17/292,362

(22) PCT Filed: Nov. 7, 2019

(86) PCT No.: PCT/CN2019/116132
§ 371 (c)(1),
(2) Date: May 7, 2021

(87) PCT Pub. No.: WO2020/094082
PCT Pub. Date: May 14, 2020

(65) Prior Publication Data
US 2022/0003709 A1    Jan. 6, 2022

(30) Foreign Application Priority Data

Nov. 8, 2018   (CN) .......................... 201811325204.7

(51) Int. Cl.
*G01N 27/327* (2006.01)
*C12N 9/80* (2006.01)

(52) U.S. Cl.
CPC ........... *G01N 27/3272* (2013.01); *C12N 9/80* (2013.01); *C12Y 305/01005* (2013.01)

(58) Field of Classification Search
CPC ............. G01N 27/327; G01N 27/3272; G01N 27/3271; G01N 27/3273; C12Q 1/00; C12Q 1/02; C12Q 1/006; C12Q 1/34; C12Q 1/54
See application file for complete search history.

(56) References Cited

U.S. PATENT DOCUMENTS 5,063,081 A   11/1991  Cozzette et al.
7,540,948 B2   6/2009  Collier et al.
(Continued)

FOREIGN PATENT DOCUMENTS

CN    103364468 A    10/2013
CN    103454321 A    12/2013
(Continued)

OTHER PUBLICATIONS

Song et al. Anal Bioanal Chem 161-168 (Year: 2017).*
(Continued)

*Primary Examiner* — Gurpreet Kaur
(74) *Attorney, Agent, or Firm* — Michael A. Whittaker

(57) ABSTRACT

Provided are a potentiometric biosensor (100) and a method for detecting urea concentration in a sample. The potentiometric biosensor (100) comprises an indication electrode (23) and a reference electrode (24). A second reaction reagent on the indication electrode (23) comprises a urease but does not comprise an electron transporter. A first reaction reagent on the reference electrode (24) comprises an electron transporter but does not comprise a urease. In the case where no external voltage is applied, after a blood sample has been added, the urease catalyzes the reaction of urea in the sample, thereby causing a potential difference between the indication electrode (23) and the reference electrode (24). Furthermore, the potential difference between the indication electrode (23) and the reference electrode (24) is in a linear relationship with the urea concentration in the (Continued)

sample, and the urea concentration in the sample can be calculated according to such linear relationship.

8 Claims, 4 Drawing Sheets

(56) References Cited

U.S. PATENT DOCUMENTS

| | | |
|---|---|---|
| 2007/0131548 A1 | 6/2007 | Winarta et al. |
| 2008/0149480 A1* | 6/2008 | Bell ........................ C12Q 1/001 204/403.14 |
| 2014/0374278 A1* | 12/2014 | Rodgers ............. G01N 27/3272 205/792 |

FOREIGN PATENT DOCUMENTS

| | | |
|---|---|---|
| CN | 109946352 A | 6/2019 |
| CN | 109946353 A | 6/2019 |
| EP | 2980573 A1 | 2/2016 |
| WO | 2020094082 A1 | 5/2020 |

OTHER PUBLICATIONS

Extended European Search Report issued in EP 19881332 dated Jul. 13, 2022 (10 pages).
International Search Report and Written Opinion issued in PCT/CN2019/116132 dated Jan. 23, 2020—incl Engl lang transl (19 pages total).
International Preliminary Report on Patentability issued in PCT/CN2019/116132 dated May 11, 2021—incl Engl lang transl (13 pages total).

* cited by examiner

POTENTIOMETRIC BIOSENSOR AND DETECTION METHOD

FIELD OF THE INVENTION

The present invention relates to a potentiometric biosensor and method for testing the urea concentration in a sample, and belongs to the field of electro-analytically chemical detection.

BACKGROUND OF THE INVENTION

Urea is a final product of catabolism of a protein and its component amino acids, and does not bind to a plasma protein. In protein catabolism, a protein is decomposed into amino acids, and ammonia formed by deamination of the amino acids enters a urea cycle in liver and produces urea together with carbon dioxide. Urea produced in the liver is mainly excreted by kidney, and a small part of it is excreted by sweat. In the kidney, urea is filtered through glomerulus and excreted from the body along with urine. If the function of the kidney is damaged, then the glomerular filtration rate (GFR) will be decreased, and the urea concentration in blood will be increased. Therefore, the urea content in the blood is one of the most important physiological indexes to evaluate the renal function, and is used for diagnosing some kidney diseases and metabolic disorders.

Urea determination is the most widely used experiment for evaluating the renal function. It is often used in combination with creatinine to diagnose prerenal hyperureaemia (cardiac decompensation, dehydration, and increased protein decomposition), renal hyperureaemia (glomerular nephritis, chronic nephritis, polycystic kidney disease, nephrosclerosis and renal tubular necrosis) and postrenal hyperureaemia (urinary tract obstruction).

Early urea determination methods are mostly colorimetric methods, for example, urea is first decomposed into $NH_4^+$ and $HCO_3^-$ with urease, then the absorbance of blue indophenol produced is tested at a wavelength of 560 nm according to the Polaises reaction, and the decrease rate of the absorbance is tested at a wavelength of 340 nm with glutamate dehydrogenase, or diacetyl monooxime is directly condensed with urea, and the absorbance of red oxazine derivatives produced is tested at a wavelength of 525 nm. However, the colorimetric methods require expensive instruments and professional technicians, the operation is cumbersome, and the results cannot be determined quickly. In addition, endogenous interferences in blood also affect the accuracy of the test results.

For this reason, U.S. Pat. Nos. 5,063,081A and 7,540,948B2 both use a potentiometric method based on an indication electrode and a reference electrode to test the urea nitrogen content in blood (that is, the nitrogen content in blood urea, which has a definite conversion relationship with the urea concentration in blood): the indication electrode is composed of a urease layer (containing enough urease) on the top, a metal/metal salt conductive layer at the bottom, and a membrane layer between the two, wherein the membrane layer contains a $NH_4^+$ selective ionophore, such as nonactin and enniatin. When blood is added, the urease reacts with urea in the blood to produce $NH_4^+$, $HCO_3^-$ and $OH^-$, and only $NH_4^+$ can pass through the membrane layer through the $NH_4^+$ selective ionophores, resulting in a potential difference between two sides of the membrane layer; and finally, the urea nitrogen content in the sample is calculated by measuring the potential difference between the indication electrode and the reference electrode. However, the potentiometric method in the two US patents also has obvious shortcomings: the $NH_4^+$ selective ionophore is expensive; according to the Nernst equation, under certain conditions, the potential difference between the indication electrode and the reference electrode has a linear relationship with the logarithm of the urea concentration in the blood, and based on this, the urea concentration in the blood is calculated, which will lead to a more complicated calculation method for the urea concentration in the blood; and the indication electrode is relatively complicated in structure, and therefore is relatively difficult to manufacture.

In addition, the Chinese patent application CN201310308122.2 provides a reagent for detecting urea nitrogen by a urease electrode method. However, its detection principle is to determine the concentration of ions in a solution based on the linear relationship between the potential and the logarithm of the activity of given ions in the solution, and then to calculate the urea nitrogen content in the solution. This calculation method is relatively complicated. In addition, because the concentration of the given ions in the solution is calculated by means of a urease electrode, the test result is prone to interference from other ions in the solution.

SUMMARY OF THE INVENTION

In view of the shortcomings of the prior art, the present invention provides a potentiometric biosensor, which includes an indication electrode and a reference electrode; the indication electrode does not contain a $NH_4^+$ selective ionophore; a first reaction reagent on the reference electrode includes a ruthenium compound (such as hexaammineruthenium(III) chloride) but does not include urease, and a second reaction reagent on the indication electrode includes urease but does not include a ruthenium compound. Unexpectedly, in the case where no external voltage is applied, after a sample such as blood is added, urease catalyzes the reaction of urea in the sample, thereby causing a potential difference between the indication electrode and the reference electrode; the potential difference between the indication electrode and the reference electrode is in a linear relationship with the urea concentration in the sample.

An object of the present invention is to provide a potentiometric biosensor with a sample addition end and an electrical connection end, the potentiometric biosensor including an insulating substrate, a conductive layer, a reaction region forming layer, a channel forming layer and an upper cover layer;

the conductive layer is disposed on the insulating substrate, and includes a first contact and a second contact that are located at the electrical connection end, an indication electrode and a reference electrode that are located at the sample addition end, a first conductive trace for connecting the reference electrode with the first contact, and a second conductive trace for connecting the indication electrode with the second contact;

the reaction region forming layer covers the electrode system and is provided with a first reaction hole and a second reaction hole that are spaced apart, the first reaction hole exposes at least a part of the reference electrode and forms a first reaction region on the reference electrode, and the second reaction hole exposes at least a part of the indication electrode and forms a second reaction region on the indication electrode;

the channel forming layer is disposed on the reaction region forming layer, is provided with an opening in the sample addition end, and the opening simultaneously exposes at least a part of the first reaction region and at least a part of the second reaction region;

the upper cover layer is disposed on the channel forming layer and is provided with a vent, the upper cover layer forms a sample channel together with the opening, the first reaction region forming layer and the insulating substrate, the vent is located above the sample channel, a sample addition port is provided in the sample addition end, and a sample enters the sample channel through the sample addition port;

a first reaction reagent is located on the first reaction region and contains an electron mediator but does not contain urease, and a second reaction reagent is located on the second reaction region and contains urease but does not contain an electron mediator.

Further, the reaction region forming layer is formed by printing a hydrophobic insulating material on the insulating substrate through a screen printing method, and during screen printing, a part of the insulating substrate is not printed with the insulating material, thereby forming the first reaction hole and the second reaction hole that are spaced apart in the reaction region forming layer.

Further, the width of the opening is 1.0 to 2.5 mm, and the widths of the second reaction region and the first reaction region are approximately 2 to 3 times the width of the opening.

Further, the first reaction reagent and the second reaction reagent further contain a polymer binder, a surfactant, a buffer, and a stabilizer; the polymer binder is a cellulose derivative, and has a concentration of 0.01-10% (w/w); the surfactant is selected from a PEG series surfactant, a Tween series surfactant, sodium cholate, CHAP, Triton X-100 or hexadecyl choline, and has a concentration of 0.01% to 5% (w/w); the buffer is selected from citric acid buffer, phosphate buffer or Tris-HCl buffer; and the stabilizer is selected from a sugar, a sugar alcohol, an amino acid, a protein or a carboxyl-containing organic acid, and has a concentration of 0.1% to 50%.

Further, the electron mediator is selected from a ruthenium compound, potassium ferricyanide or potassium ferrocyanide.

Further, the electron mediator has a concentration of 1.0-4.5% (w/w).

Further, the electron mediator is a ruthenium compound; and the ruthenium compound has a concentration of 1.0-4.5% (w/w).

Further, the urease has a concentration of 2280 to 8712 U/mL.

Further, at least one auxiliary diffusion component is disposed on one or two sides of the reference electrode and the indication electrode; each auxiliary diffusion component disposed on one or two sides of the reference electrode partially covers the first reaction region, and each auxiliary diffusion component disposed on one or two sides of the indication electrode partially covers the second reaction region.

Further, the auxiliary diffusion component is a porous material made of conductive carbon ink.

Further, the spacing distance between the auxiliary diffusion component closest to any of the two opposite sides of the reference electrode and the reference electrode and the spacing distance between the auxiliary diffusion component closest to any of the two opposite sides of the indication electrode and the indication electrode are 0.1 to 0.5 mm.

An object of the present invention is also to provide a method for testing the urea concentration in a sample, providing a potentiometric biosensor with a sample addition end and an electrical connection end, wherein the potentiometric biosensor includes a first contact and a second contact that are located at the electrical connection end and includes an indication electrode and a reference electrode that are at the sample addition end, the reaction reagent includes a first reaction reagent on the reference electrode and a second reaction reagent on the indication electrode, the first reaction reagent contains an electron mediator but does not contain urease, and the second reaction reagent contains urease but does not contain an electron mediator; a sample addition port is provided in the sample addition end, and the method includes the following steps:

(1) inserting the potentiometric biosensor into an electrical connector of a test instrument through the first contact and the second contact;

(2) adding the sample to the sample addition port of the potentiometric biosensor, and allowing the sample to chemically react with the first reaction reagent and the second reaction reagent; and (3) testing the potential difference between the indication electrode and the reference electrode by means of an open-circuit potentiometric method, and in view of the direct linear relationship between the tested potential difference and the urea concentration in the sample, determining the urea concentration in the sample based on the potential difference.

Further, the first reaction reagent and the second reaction reagent further contain a polymer binder, a surfactant, a buffer, and a stabilizer; the polymer binder is a cellulose derivative, and has a concentration of 0.01-10% (W/W); the surfactant is selected from a PEG series surfactant, a Tween series surfactant, sodium cholate, CHAP, Triton X-100 or hexadecyl choline, and has a concentration of 0.01% to 5% (W/W); the buffer is selected from citric acid buffer, phosphate buffer or Tris-HCl buffer; and the stabilizer is selected from a sugar, a sugar alcohol, an amino acid, a protein or a carboxyl-containing organic acid, and has a concentration of 0.1% to 50%.

Further, the electron mediator is selected from a ruthenium compound, potassium ferricyanide or potassium ferrocyanide.

Further, the ruthenium compound has a chemical structural formula $[Ru(NH_3)_5X]^{n+}$, X is selected from $NH_3$, halogen ions, CN, pyridine or nicotinamide, and n is 2 or 3.

Further, the ruthenium compound is $[Ru(NH_3)_6]Cl_3$.

Further, the electron mediator has a concentration of 1.0-4.5% (w/w).

Further, the electron mediator is a ruthenium compound; and the ruthenium compound has a concentration of 1.0-4.5% (w/w).

Further, the urease has a concentration of 2280 to 8712 U/mL.

An object of the present invention is also to provide a reaction reagent for testing the urea concentration in a sample by means of a potentiometric biosensor, wherein the potentiometric biosensor includes an indication electrode and a reference electrode, the reaction reagent includes a first reaction reagent on the reference electrode and a second reaction reagent on the indication electrode, the first reaction reagent contains an electron mediator but does not contain urease, and the second reaction reagent contains urease but does not contain an electron mediator.

Further, the urease has a concentration of 2280 to 8712 U/mL.

Further, the first reaction reagent and the second reaction reagent further contain a polymer binder, a surfactant, a buffer, and a stabilizer.

Further, the polymer binder is a cellulose derivative, and has a concentration of 0.01-10% (W/W); the surfactant is selected from a PEG series surfactant, a Tween series surfactant, sodium cholate, CHAP, Triton X-100 or hexadecyl choline, and has a concentration of 0.01% to 5% (W/W); the buffer is selected from citric acid buffer, phosphate buffer or Tris-HCl buffer; and the stabilizer is selected from a sugar, a sugar alcohol, an amino acid, a protein or a carboxyl-containing organic acid, and has a concentration of 0.1% to 50%.

Further, the electron mediator has a concentration of 1.0-4.5% (w/w).

Further, the electron mediator is a ruthenium compound.

Further, the present invention also includes an application of the reaction reagent for testing the urea concentration in the sample on the potentiometric biosensor.

Further, the present invention also includes an application of the reaction reagent for testing the urea concentration in the sample in the method for testing the urea concentration in the sample by the potentiometric biosensor.

An object of the present invention is also to provide a method for testing the urea concentration in a sample, including the following steps: (1) providing a potentiometric biosensor, wherein the potentiometric biosensor includes a first electrode and a second electrode, the reaction reagent includes a first reaction reagent on the first electrode and a second reaction reagent on the second electrode, the first reaction reagent contains an electron mediator but does not contain urease, and the second reaction reagent contains urease but does not contain an electron mediator;

(2) inserting the potentiometric biosensor into a test instrument;

(3) adding the sample to the potentiometric biosensor, and allowing the sample to chemically react with the first reaction reagent and the second reaction reagent; and (4) testing the potential difference between the first electrode and the second electrode by means of the test instrument and an open-circuit potentiometric method, and in view of the direct linear relationship between the tested potential difference and the urea concentration in the sample, determining the urea concentration in the sample based on the potential difference.

An object of the present invention is also to provide a reaction reagent for testing the urea concentration in a sample by means of a potentiometric biosensor, wherein the potentiometric biosensor includes a first electrode and a second electrode, the reaction reagent includes a first reaction reagent on the first electrode and a second reaction reagent on the second electrode, the first reaction reagent contains an electron mediator but does not contain urease, and the second reaction reagent contains urease but does not contain an electron mediator.

An object of the present invention is also to provide a potentiometric biosensor, the potentiometric biosensor including a first electrode and a second electrode, wherein the reaction reagent includes a first reaction reagent on the first electrode and a second reaction reagent on the second electrode, the first reaction reagent contains an electron mediator but does not contain urease, and the second reaction reagent contains urease but does not contain an electron mediator.

Further, the first electrode is a reference electrode, and the second electrode is an indication electrode or a working electrode.

The beneficial effects of the present invention are as follows: (1) the present invention does not use the high-cost $NH_4^+$ selective ionophore in the prior art, so that the test cost is greatly reduced, and the indication electrode is simpler in structure and convenient to manufacture in large scale; (2) the existing testing method considers that the produced potential difference has a linear relationship with the logarithmic value of the urea concentration in the sample, or after the sample is added and a voltage is applied between the indication electrode and the reference electrode, the produced current value has a linear relationship with the urea concentration in the sample; however, in the potentiometric biosensor provided by the present invention, the indication electrode contains urease but does not contain an electron mediator, and the reference electrode contains an electron mediator but does not contain urease; in the case where no external voltage is applied, after the sample is added, if the sample contains urea, the urease catalyzes the reaction of the urea in the sample, and a potential difference is produced between the indication electrode and the reference electrode; in addition, the produced potential difference has a good linear relationship with the urea in the sample, and the urea concentration in the sample is calculated; therefore, the present invention tests the urea in the sample more simply without complicated calculation steps and circuit design, so the test result is more accurate; and (3) the test result of the present invention has a good ability to resist HCT (hematocrit) interference: under the same urea concentration, the measured values of potential differences in the cases of 30% and 60% of HCT are different from the measured value of the potential difference in the case of 42% of hematocrit within a range of 10%, so HCT has little interference to the test result.

DETAILED DESCRIPTION OF EMBODIMENTS

Figure 1:
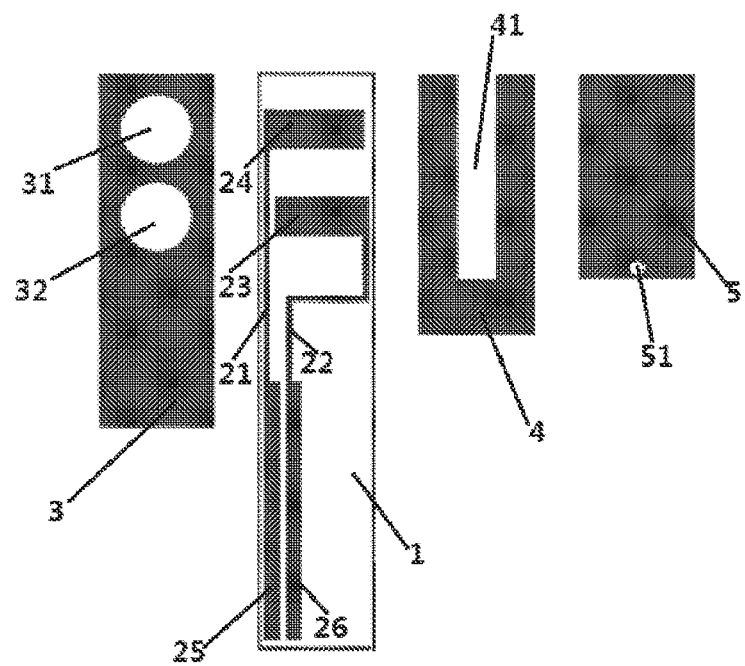
FIG. 1 is an exploded view of an embodiment of a potentiometric biosensor according to the present invention.
Figure 3:
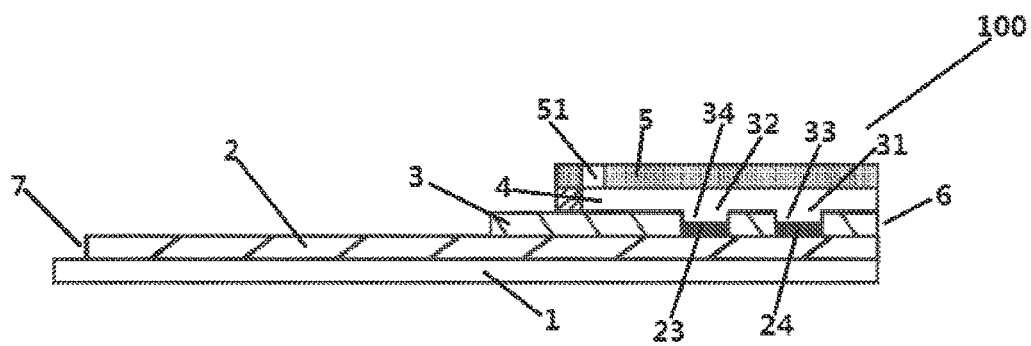
FIG. 3 is a lateral schematic diagram of an embodiment of the potentiometric biosensor according to the present invention.
Figure 4:
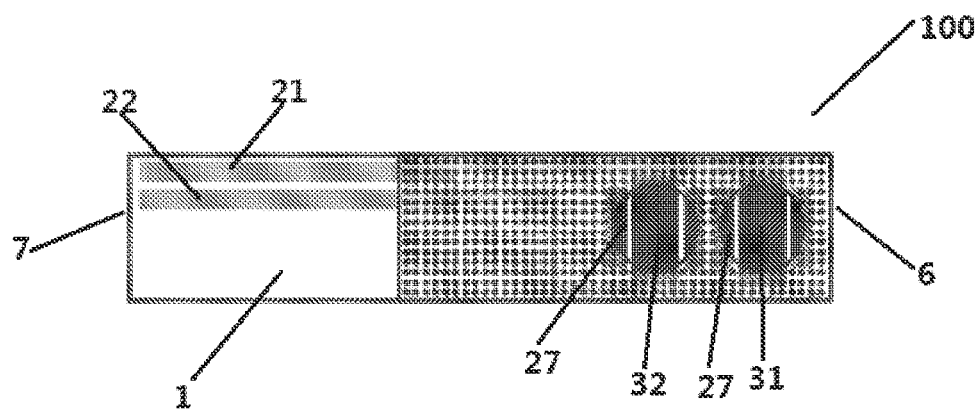
FIG. 4 is an overall structure diagram of an embodiment of the potentiometric biosensor according to the present invention.

When a potentiometric biosensor of the present invention is used to test urea in a sample such as blood, as shown in FIGS. 1, 3 and 4, the potentiometric biosensor (also referred to as a test strip) 100 is of a layered structure with a sample addition end 6 and an electrical connection end 7, and includes an insulating substrate 1, a conductive layer 2, a reaction region forming layer 3, a channel forming layer 4, and an upper cover layer 5. The insulating substrate 1, the reaction region forming layer 3, the channel forming layer 4 and the upper cover layer 5 are all made of insulating materials. Preferred insulating materials are polyvinyl chloride (PVC) polycarbonate, polysulfone resin, nylon plastic, polyurethane, nitrocellulose, cellulose propionate, cellulose acetate, cellulose acetate butyrate, polyester fiber, polyimide, polypropylene, polyethylene and polystyrene. The components of the potentiometric biosensor can be laminated together, or bonded together with an adhesive, or the reaction region forming layer 3, the channel forming layer 4 and the upper cover layer 5 can be sequentially printed on the insulating substrate 1 by screen printing, Preferably, the surface of the upper cover layer 5 in contact with the channel forming layer 4 is coated with a layer of hydrophilic material. A common hydrophilic material is starch, polysaccharides, cellulose molecules, polyacrylic acid, polyacrylamide, polyvinyl alcohol, polyurethane and polyamide, etc.

The conductive layer 2 is disposed on the insulating substrate 1. A first conductive trace 21 and a second conductive trace 22 are formed by scribing or scoring the conductive layer 2, or a first conductive trace 21 and a second conductive trace 22 are printed on the insulating substrate 1 by screen printing. Preferably, the scribing or scoring may be performed by laser. Of course, more conductive traces may be provided on the insulating substrate 1 as required. The conductive layer 2 may be made of any conductive material, such as a carbon film, gold, silver, tin oxides/gold, platinum, other noble metals, or oxides thereof. The conductive layer 2 further includes at least two conductive contacts at the electrical connection end 7: a first contact 25 and a second contact 26; and an electrode system located at the sample addition end 6, wherein the electrode system includes an indication electrode (also referred to as a working electrode) 23 and a reference electrode 24, the second conductive trace 22 connects the indication electrode 23 with the second contact 26, and the first conductive trace 21 connects the reference electrode 24 with the first contact 25. Of course, according to actual needs, the electrode system may include other electrodes, such as an HCT electrode, the HCT electrode can test an impedance value of a blood sample with the indication electrode 23, and HCT value of the sample can be calculated according to the tested impedance value. The electrode system may also include a pair of specific HCT electrodes, which are directly used to test an HCT value of a blood sample. The electrode system may also include at least one sample judging electrode for judging whether the blood sample added is sufficient. It should be noted that the reference electrode 24 can be replaced with a counter electrode.

The reaction region forming layer 3 covers the electrode system and is provided with two spaced-apart reaction holes: a first reaction hole 31 and a second reaction hole 32. The shapes of the first reaction hole 31 and the second reaction hole 32 may be selected from geometric shapes, such as rectangles, ellipses, circles, or corner-cut rectangles. The second reaction hole 32 exposes a part or all of the indication electrode 23, and forms a second reaction region 34 on the indication electrode 23. The first reaction hole 31 exposes a part or all of the reference electrode 24, and forms a first reaction region 33 on the reference electrode 24. In addition to covering the electrode system, the reaction region forming layer 3 can also extend to the electrical connection end 7, so as to partially or completely cover the first conductive trace 21 and the second conductive trace 22. In addition, the reaction region forming layer 3 can also continue to extend to the electrical connection end 7, so as to partially cover the first contact 25 and the second contact 26, but not to fully cover the first contact 25 and the second contact 26, which ensures that the first contact 25 and the second contact 26 can be connected to a test instrument that is used for measuring the potential difference between the indication electrode 23 and the reference electrode 24, thereby ensuring that an open circuit is formed between the indication electrode 23 and the reference electrode 24, the first conductive trace 21 and the second conductive trace 22, the first contact 25 and the second contact 26, and the internal circuit of the test instrument, and the potential difference between the indication electrode 23 and the reference electrode 24 can be measured after a blood sample is added.

Preferably, the reaction region forming layer 3 is formed by printing a hydrophobic insulating material (such as insulating ink) on the insulating substrate 1 through a screen printing method, and during screen printing, a part of the insulating substrate 1 is not printed with the insulating material, so that two spaced apart reaction holes are formed in the reaction region forming layer 3: a first reaction hole 31 and a second reaction hole 32. The advantage of this is that in the reaction region forming layer 3, the outsides of the first reaction hole 31 and the second reaction hole 32 are the hydrophobic insulating material (preferably insulating ink), then when a first reaction reagent is added to the first reaction region 33 and a second reaction reagent is added to the second reaction region 34, the first reaction reagent only diffuses within the first reaction region 33 and does not diffuse to the outside of the first reaction region 33, and the second reaction reagent only diffuses in the second reaction region 34 and does not diffuse to the outside of the second reaction region 34, thereby avoiding overflow of the first reaction reagent to the outside of the first reaction region 33 and overflow of the second reaction reagent to the outside of the second reaction region 34 to cause differences in quantities of the reaction agents in the first reaction region 33 and the second reaction region 34 between different potentiometric biosensors of the same batch or between different potentiometric biosensors of different batches so as to cause inaccurate test results.

In addition, the reaction region forming layer 3 may also be a double-sided tape or a single-sided tape, so that the reaction region forming layer 3 is adhered to the insulating substrate 1. Moreover, the reaction region forming layer 3 may also be supported by a plastic sheet, and then coated with a pressure-sensitive adhesive or photosensitive polymer on one side thereof, wherein the photosensitive polymer is bonded to the insulating substrate 1 under the action of ultrasonic waves.

The second reaction region 34 on the indication electrode 23 contains a second reaction reagent. The first reaction region 33 on the reference electrode 24 contains a first reaction reagent. The second reaction reagent and the first reaction reagent can be respectively added to the second reaction hole 32 and the first reaction hole 31 by means of dripping or screen printing.

The channel forming layer 4 is disposed on the reaction region forming layer 3, and covers the second reaction region 34 on the indication electrode 23 and the first reaction region 33 on the reference electrode 24. The channel forming layer 4 has an opening 41 at the sample addition end 6. The opening 41 is located above the second reaction region 34 on the indication electrode 23 and the first reaction region 33 on the reference electrode 24, so that the second reaction region 34 on the indication electrode 23 and the first reaction region 33 on the reference electrode 24 are at least partially exposed. The shape of the opening 41 may be a rectangle, a U shape, an ellipse, a circle, a corner-cut rectangle (that is, a rectangle with arc-shaped corners), etc. The opening 41 extends directly to the sample addition end 6. The width of the opening 41 is preferably 1.0 to 2.5 mm, and the widths of the second reaction region 34 on the indication electrode 23 and the first reaction region 33 on the reference electrode 24 are approximately 2 to 3 times the width of the opening 41, which ensures that the added sample is mostly concentrated in the first reaction region 33 and the second reaction region 34, and less remains in the opening 41, so that the first reaction reagent on the first reaction region 33 and the second reaction reagent on the second reaction region 34 are dissolved faster, the test time is reduced, and the amount of the sample can be reduced. The channel forming layer 4 may be a double-sided tape, so that the channel forming layer 4 is adhered to the reaction region forming layer 3. In addition, the channel forming layer 4 may also be supported by a plastic sheet, and then coated with a pressure-sensitive adhesive or photosensitive polymer on one side thereof, wherein the photosensitive polymer is bonded to the reaction region forming layer 3 under the action of ultrasonic waves. In addition, the channel forming layer 4 can also be printed on the reaction region forming layer 3 by a screen printing method.

The upper cover layer 5 is disposed on the channel forming layer 4, and covers the opening 41 of the channel forming layer 4. The upper cover layer 5, the opening 41 of the channel forming layer 4, the reaction region forming layer 3 and the insulating substrate 1 together form a sample channel. The upper cover layer 5 has a vent 51, and the vent 51 is located above the sample channel, and is used for exhausting air in the sample channel during sample addition. A sample addition port is located at the sample addition end 6 of the potentiometric biosensor 100, and the sample addition port is communicated with the sample channel, which means that when a sample is added to the sample addition port, the sample enters the sample channel through the sample addition port under capillary action, to dissolve the first reaction reagent on the reference electrode 24 and the second reaction reagent on the indication electrode 23.

The first contact 25 and the second contact 26 at the electrical connection end 7 are inserted into an electrical connector of a test instrument, the potentiometric biosensor 100 is electrically connected to the test instrument, then a blood sample is added, the blood sample chemically reacts with the first reaction reagent on the reference electrode 24 and the second reaction reagent on the indication electrode 2 to cause a potential difference between the indication electrode 23 and the reference electrode 24, and the potential difference can be tested through the test instrument. The potential difference has a linear relationship with the urea concentration in the sample. According to the pre-determined standard curve, the urea concentration in the sample can be quickly calculated. Meanwhile, since the inventors found the difference in the present invention from the prior art that the urea concentration in a sample such as blood directly has a linear relationship with the tested potential difference, an intermediate step of calculating a logarithmic value of the urea concentration is not required, and the measured value of urea can be obtained without complicated calculation and conversion when the urea concentration in the sample is tested by means of the potential difference.

The second reaction reagent on the indication electrode 23 includes urease but does not include an electron mediator, and preferably further includes at least a polymer binder, a surfactant, and a buffer. The first reaction reagent on the reference electrode 24 includes an electron mediator but does not include urease, and preferably further includes at least a polymer binder, a surfactant, and a buffer.

Figure 2:
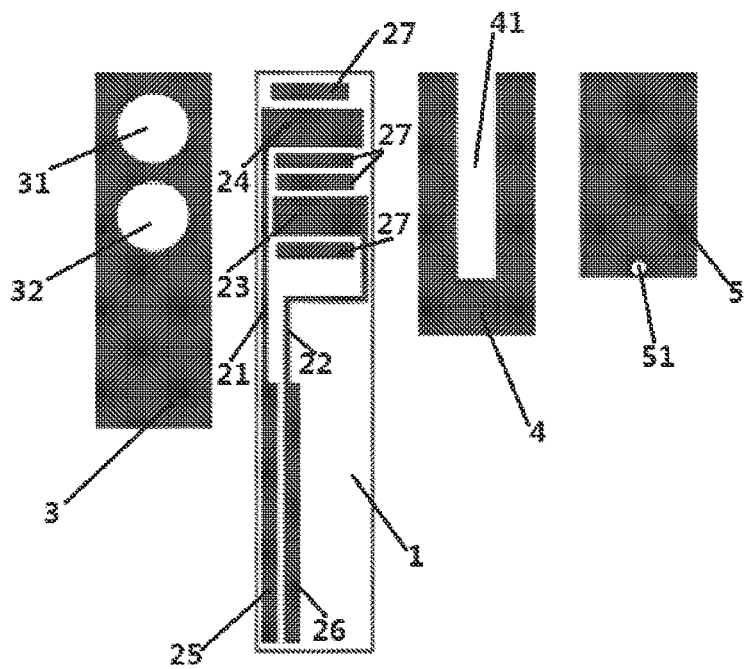
FIG. 2 is an exploded view of another embodiment of a potentiometric biosensor according to the present invention.
Figure 5:
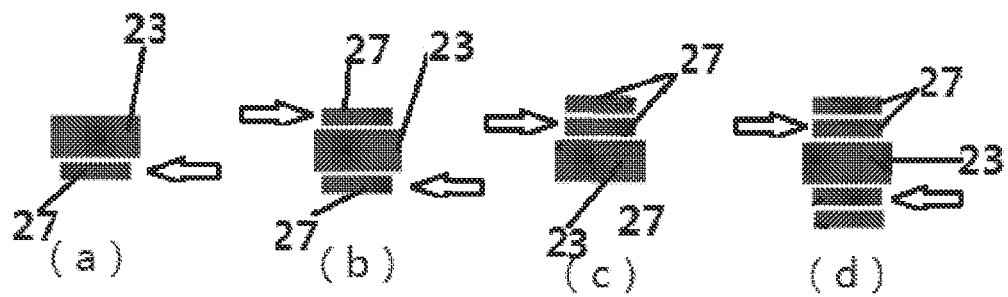
FIG. 5 shows multiple distribution modes of at least one auxiliary diffusion component on two sides of an indication electrode, where (a) shows one auxiliary diffusion component is disposed on the lower side of the indication electrode; (b) shows one auxiliary diffusion component is disposed on each of two sides (upper side and lower side) of the indication electrode; (c) shows two auxiliary diffusion components are disposed on the upper side of the indication electrode; and (d) shows two auxiliary diffusion components are disposed on each of the upper side and lower side of the indication electrode.

As shown in FIG. 2, the conductive layer 2 further includes a plurality of auxiliary diffusion components 27. Specifically, at least one auxiliary diffusion component 27 is disposed on two sides of the indication electrode 23, and at least one auxiliary diffusion component 27 is disposed on two sides of the reference electrode 24. These auxiliary diffusion components 27 are a porous material manufactured from conductive carbon ink, and their function is to, when the second reaction reagent solution is added to the second reaction region 34 on the indication electrode 23 and the first reaction reagent solution is added to the first reaction region 33 on the reference electrode 24, facilitate the rapid and uniform diffusion of these reaction reagent solutions on these reaction regions. Of course, at least one auxiliary diffusion component 27 can also be disposed only on one side of the indication electrode 23 and/or the reference electrode 2 as required. No matter whether at least one (such as 1, 2, 3 or more, preferably 1 or 2) auxiliary diffusion component 27 is provided on two sides of the indication electrode 23 or at least one (such as 1, 2, 3 or more, preferably 1 or 2) auxiliary diffusion component 27 is provided only on one side of the indication electrode 23, at least a part of each auxiliary diffusion component 27 covers the second reaction region 34 on the indication electrode 23. As shown in FIGS. 5(a) and 5(c), when at least one auxiliary diffusion component 27 is provided only on one side of the indication electrode 23, the spacing distance between the auxiliary diffusion component 27 closest to the indication electrode 23 (the auxiliary diffusion component indicated by the white arrow in FIGS. 5(a) and 5(c)) and the indication electrode 23 is 0.1 to 0.5 mm, preferably 0.25 to 0.4 mm. As shown in FIGS. 5(b) and 5(d), when at least one auxiliary diffusion component 27 is provided on each of two opposite sides (such as an upper side and a lower side) of the indication electrode 23, the spacing distance between the auxiliary diffusion component 27 closest to the upper side of the indication electrode 23 (the auxiliary diffusion component indicated by the white arrow pointing to the right in FIGS. 5(b) and 5(d)) and the indication electrode 23, and the spacing distance between the auxiliary diffusion component 27 closest to the lower side of the indication electrode 23 (the auxiliary diffusion component indicated by the white arrow pointing to the left in FIGS. 5(b) and 5(d)) and the indication electrode 23, are both 0.1 to 0.5 mm, preferably 0.25 to 0.4 mm. This spacing distance can ensure that the second reaction reagent solution is diffused more quickly and more uniformly on the second reaction region 34.

Figure 6:
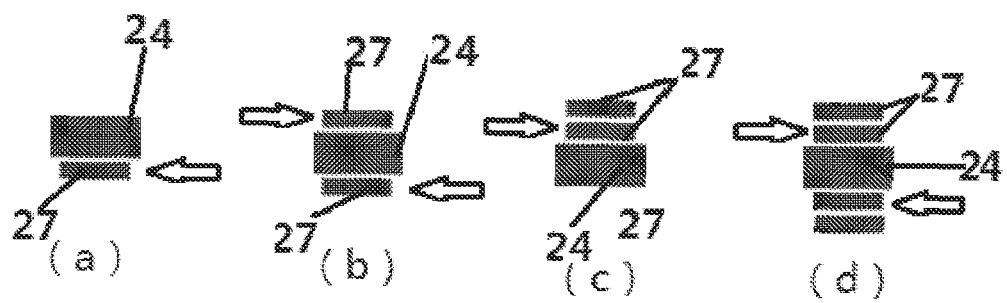
FIG. 6 shows multiple distribution modes of at least one auxiliary diffusion component on two sides of a reference electrode, where (a) shows one auxiliary diffusion component is disposed on the lower side of the reference electrode; (b) shows one auxiliary diffusion component is disposed on each of two sides (upper side and lower side) of the reference electrode; (c) shows two auxiliary diffusion components are disposed on the upper side of the reference electrode; and (d) shows two auxiliary diffusion components are disposed on each of the upper side and lower side of the reference electrode.

Similarly, no matter whether at least one (such as 1, 2, 3 or more, preferably 1 or 2) auxiliary diffusion component 27 is provided on each of two sides of the reference electrode 24 or at least one (such as 1, 2, 3 or more, preferably 1 or 2) auxiliary diffusion component 27 is provided only on one side of the reference electrode 24, at least a part of each auxiliary diffusion component 27 covers the first reaction region 33 on the reference electrode 24. As shown in FIGS. 6(a) and 6(c), when at least one auxiliary diffusion component 27 is provided only on one side of the reference electrode 24, the spacing distance between the auxiliary diffusion component 27 closest to the reference electrode 24 (the auxiliary diffusion component indicated by the white arrow in FIGS. 6(a) and 6(c)) and the reference electrode 24 is 0.1 to 0.5 mm, preferably 0.25 to 0.4 mm. As shown in FIGS. 6(b) and 6(d), when at least one auxiliary diffusion component 27 is provided on each of two opposite sides (such as an upper side and a lower side) of the reference electrode 24, the spacing distance between the auxiliary diffusion component 27 closest to the upper side of the reference electrode 24 (the auxiliary diffusion component indicated by the white arrow pointing to the right in FIGS. 6(b) and 6(d)) and the reference electrode 24, and the spacing distance between the auxiliary diffusion component 27 closest to the lower side of the reference electrode 24 (the auxiliary diffusion component indicated by the white arrow pointing to the left in FIGS. 6(b) and 6(d)) and the reference electrode 24, are both 0.1 to 0.5 mm, preferably 0.25 to 0.4 mm. This spacing distance can ensure that the first reaction reagent solution is diffused more quickly and more uniformly on the first reaction region 33.

As the urea concentration in a sample such as blood is tested, the concentration of the urease in the second reaction reagent on the indication electrode 23 is preferably 2280 to 8712 U/mL.

In conventional electrochemical detection, the function of the electron mediator is to promote the transfer of electrons from an enzymatic reaction to an electrode when a voltage is applied to the electrode system. However, in the present invention, during the detection, no voltage is applied to the indication electrode and the reference electrode to detect the resulting current, but the potential difference generated between the indication electrode and the reference electrode during the reaction is detected, so the function of the electron mediator is not to promote electron transfer. The present invention also found that if the electron mediator is not added to the reference electrode, almost no potential difference will be detected; and when the electron mediator is added to both the indication electrode and the reference electrode, the slope of a standard curve produced is much less than 1, and there is a poor potential difference gradient, which will affect the accuracy of the test results. However, the specific effect of the electron mediator in the present invention is currently unknown. The electron mediator used in the present invention is preferably selected from iron compounds, osmium compounds or ruthenium compounds, wherein the iron compounds include potassium ferricyanide ($K_3Fe(CN)_6$), potassium ferrocyanide ($K_4Fe(CN)_6$), ferrocene and derivatives thereof; the osmium compounds include dipyridine osmium complexes and derivatives thereof; and the ruthenium compounds may be selected from ruthenium complexes, for example, with a chemical structural formula $[Ru(NH_3)_5X]^{n+}$, where X includes $NH_3$, halogen ions, CN, pyridine or nicotinamide, n is 2 or 3, and preferably, X is selected from $NH_3$ or halogen ions. Preferably, the ruthenium compound is hexaammineruthenium (III) chloride ($[Ru(NH_3)_6]Cl_3$).

The polymer binder should have good water solubility, and should also be able to bind other chemical reagents in the second reaction reagent on the indication electrode and the first reaction reagent on the reference electrode, so as to keep these reaction reagents stable. The polymer binder is preferably a cellulose derivative, such as methyl cellulose, hydroxyethyl cellulose, hydroxymethyl cellulose, or cellulose acetate, and its concentration is preferably 0.01-10% (w/w).

The surfactant functions to promote the diffusion of the added first reaction reagent solution and second reaction reagent solution in the first reaction region 33 and the second reaction region 34 respectively, and to quickly dissolve, when a sample is added, the first reaction reagent and the second reaction reagent in the form of solids on the first reaction region 33 and the second reaction region 34. The surfactant may be selected from anionic surfactant, nonionic surfactant or cationic surfactant, such as PEG series surfactant, Tween series surfactant (Tween-20, Tween-21, Tween-40, Tween-60, Tween-61, Tween-80, Tween-81, and Tween-85), sodium cholate, CHAP, Triton X-100 and hexadecyl choline. The concentration of the surfactant used is usually 0.01% to 5% (W/W).

The buffer may also be included in the first reaction reagent and the second reaction reagent. The buffer should be kept in a sufficient amount to keep the pH value of the reaction mixture within an appropriate range when the sample is added, thereby ensuring that the catalytic activity of the urease is at a high level. The buffer may be selected from citric acid buffer, phosphate buffer or Tris-HCl buffer, with pH value of 6.0 to 7.5. In the present invention, the PBS buffer used has a concentration of 0.01 to 0.5 M and pH value of 6.0 to 7.5.

The stabilizer may also be added to the first reaction reagent and the second reaction reagent, and its function is to help keep the first reaction reagent and the second reaction reagent stable and have a longer storage period. The stabilizer may be selected from a sugar or a sugar alcohol (e.g., sucrose, fucose, mannitol, sorbitol, trehalose, lactose, etc.), an amino acid, a protein (e.g., BSA and casein, etc.) or a carboxyl-containing organic acid (e.g., EDTA, etc.), and its concentration is usually 0.1% to 50% (w/w). In the present invention, the stabilizer used is trehalose with a concentration of 0.25% to 1% (w/w).

The following embodiments further describe the present invention. These embodiments are not used to limit the scope of the present invention, but to provide a further understanding of the present invention.

Embodiment 1 Preparation of Reaction Reagents

The second reaction reagent on the indication electrode and the first reaction reagent on the reference electrode according to the present invention are prepared as follows: Reaction reagents of the present invention: the second reaction reagent on the indication electrode contains 0.05-0.5 M PBS (pH 6.0-7.5), trehalose 0.25%-1% (w/w), Triton X-100 0.1%-0.6% (v/v), and urease (2280-8712 U/mL); and the first reaction reagent on the reference electrode contains 0.05-0.5 M PBS (pH 6.0-7.5), Triton X-100 0.1%-0.6% (v/v), trehalose 0.25%-1% (w/w), and hexaammineruthenium(III) chloride [$Ru(NH_3)_6$]$Cl_3$, potassium ferricyanide $K_3[Fe(CN)_6]$ or potassium ferrocyanide $K_4[Fe(CN)_6]$ 1.0 to 4.5% (w/w).

Reaction reagent 1 of the present invention: the second reaction reagent on the indication electrode contains 0.1 M PBS (pH 7.2), trehalose 1%, Triton X-100 1%, and urease (4491.2 U/ml); and the first reaction reagent on the reference electrode contains 0.1 M PBS (pH 7.2), Triton X-100 1%, trehalose 1%, and hexaammineruthenium(III) chloride (2.2%).

Reaction reagent 2 of the present invention: the second reaction reagent on the indication electrode contains 0.1 M PBS (pH 7.2), trehalose, Triton X-100, and urease (4491.2 U/ml); and the first reaction reagent on the reference electrode contains 0.1 M PBS (pH 7.2), Triton X-100 1%, trehalose 1%, and potassium ferricyanide $K_3[Fe(CN)_6]$ (2.2%).

Reaction reagent 3 of the present invention: the second reaction reagent on the indication electrode contains 0.1 M PBS (pH 7.2), trehalose, Triton X-100, and urease (4491.2 U/ml); and the first reaction reagent on the reference electrode contains 0.1 M PBS (pH 7.2), Triton X-100 1%, trehalose 1%, and potassium ferrocyanide $K_4[Fe(CN)_6]$ (2.2%).

Comparative Reaction Reagent 1:

The second reaction reagent on the indication electrode contains 0.1 M PBS (pH 7.2), trehalose 1%, Triton X-100 1%, and urease (4491.2 U/ml); and the first reaction reagent on the reference electrode contains 0.1 M PBS (pH 7.2), Triton X-100 1%, and trehalose 1%.

Comparative Reaction Reagent 2:

The second reaction reagent on the indication electrode contains 0.1 M PBS (pH 7.2), trehalose 1%, Triton X-100 1%, urease (4491.2 U/ml), and hexaammineruthenium(III) chloride (2.2%); and the first reaction reagent on the reference electrode contains 0.1 M PBS (pH 7.2), Triton X-100 1%, trehalose 1%, and hexaammineruthenium(III) chloride (2.2%).

Embodiment 2: Test of Potential Difference

Blood sample is tested with the potentiometric biosensor as shown in FIG. 1 or 2 (here, taking the potentiometric biosensor in FIG. 2 as an example). The blood sample may be selected from plasma, serum or whole blood. The whole blood sample is taken as an example here for description. The detailed steps are as follows:

(1) The electrical connection end of the potentiometric biosensor is inserted into an electrical connector of a test instrument (there are many types of test instruments, and an electrochemical workstation Biologic VSPEC-Lab (purchased from Biologic Science Instruments) is taken as an example here for description) through the first contact and the second contact of the potentiometric biosensor;

(2) Whole blood samples with multiple different urea concentrations (four different concentrations 4.5 mM, 14.5 mM, 24.5 mM and 41.5 mM here) are selected, each whole blood sample is added to the sample addition port of the potentiometric biosensor in the case where no external voltage is applied to the indication electrode and the reference electrode, and each whole blood sample is allowed to chemically react with the first reaction reagent and the second reaction reagent;

(3) The potential difference between the indication electrode and the reference electrode in the potentiometric biosensor is detected by means of an open-circuit potentiometric method; and (4) Each whole blood sample with different urea concentration is tested multiple times (usually 3 to 5 times) in parallel, and then an average value of the potential differences obtained in multiple measurements is calculated. In view of the linear relationship between the urea concentration in the sample such as blood and the tested potential difference, a linear equation between the two can be obtained.

Figure 7:
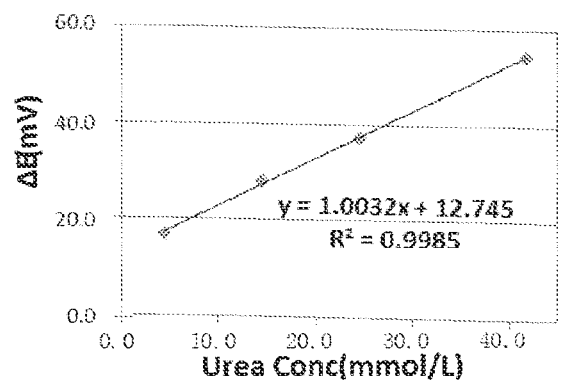
FIG. 7 is a diagram of test results obtained by a potentiometric method when a reaction reagent 1 of the present invention in Embodiment 1 is added to reaction regions of the indication electrode and the reference electrode.

When the second reaction reagent on the indication electrode and the first reaction reagent on the reference electrode are selected from the reaction reagent 1 of the present invention in Embodiment 1, the test results are shown in Table 1 and FIG. 7 and the linear equation obtained is $y=1.0032x+12.745 (R^2=0.9985)$. It can be seen from Table 1 and FIG. 7 that when only the reaction region of the reference electrode is added with the ruthenium compound as an electron mediator, $R^2>0.98$, CVs of the four parallel measurements are less than 7.5%, the potential differences measured for the whole blood samples with different urea concentrations have a good gradient (the slope of the linear equation is more than 1), and the relative deviations of the potential difference values obtained in multiple parallel measurements are small, so the measurements are comparatively accurate.

TABLE 1

| | Hematocrit (HCT) 42% | | | |
| | Urea concentration (mM) | | | |
| | 4.5 | 14.5 | 24.5 | 41.5 |
| Test result | Potential difference ΔE (mV) | | | |
| --- | --- | --- | --- | --- |
| Rep. 1 | 17.8 | 28.5 | 36.6 | 54.2 |
| Rep. 2 | 17.2 | 29.1 | 37.2 | 51.1 |
| Rep. 3 | 16.5 | 26.6 | 35.8 | 56.8 |
| Rep. 4 | 15.3 | 28.4 | 39.1 | 54.8 |
| Average value | 16.70 | 28.15 | 37.18 | 54.23 |
| SD | 1.07 | 1.08 | 1.41 | 2.36 |
| CV | 6.4% | 3.8% | 3.8% | 4.4% |

Figure 8:
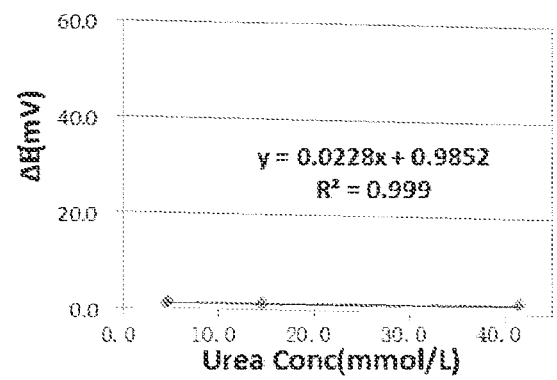
FIG. 8 is a diagram of test results obtained by a potentiometric method when a comparative reaction reagent 1 in Embodiment 1 is added to the reaction regions of the indication electrode and the reference electrode.

Meanwhile, when the second reaction reagent on the indication electrode and the first reaction reagent on the reference electrode are selected from the comparative reaction reagent 1 in Embodiment 1, the test results are shown in Table 20 and FIG. 8. It can be seen from Table 2 and FIG. 8 that when the reaction region on the indication electrode and the reaction region on the reference electrode are not added with the ruthenium compound as an electron mediator, $R^2>0.98$, CVs of the four parallel measurements are all more than 10%, and especially when the urea concentration is 4.5 mM, the CV is up to 34.5%; therefore, the relative deviations of the potential difference values obtained in multiple parallel measurements are comparatively large, and the measurements are not accurate; in addition, the potential difference values measured for different urea concentrations are relatively small, have poor gradient (the slope of the linear equation is 0.0228, which is less than 0.3), and cannot be effectively distinguished from each other. Finally, compared to Table 1 and Table 3, the potential difference values measured under different urea concentrations in Table 2 are significantly smaller and can be ignored. Considering the influence of background signals, almost no valid electrical signal is detected.

TABLE 2

| Test Result | Hematocrit (HCT) 42% Urea concentration (mM) | | |
|---|---|---|---|
| | 4.5 | 14.5 | 41.5 |
| | Potential difference ΔE (mV) | | |
| Rep. 1 | 0.9 | 1.0 | 2.2 |
| Rep. 2 | 1.7 | 1.4 | 2.1 |
| Rep. 3 | 0.9 | 1.5 | 1.7 |
| Rep. 4 | 0.9 | 1.2 | 1.7 |
| Average value | 1.10 | 1.30 | 1.93 |
| SD | 0.38 | 0.23 | 0.25 |
| CV | 34.5% | 17.7% | 13.0% |

Figure 9:
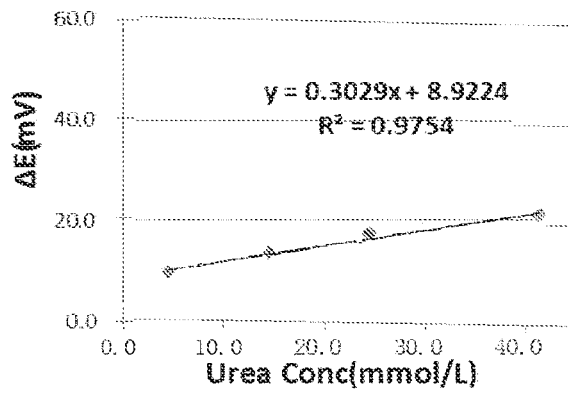
FIG. 9 is a diagram of test results obtained by a potentiometric method when a comparative reaction reagent 2 in Embodiment 1 is added to the reaction regions of the indication electrode and the reference electrode.

Moreover, when the second reaction reagent on the indication electrode and the first reaction reagent on the reference electrode are selected from the comparative reaction reagent 2 in Embodiment 1, the test results are shown in Table 3 and FIG. 9. It can be seen from Table 3 and FIG. 9 that when the reaction region of the indication electrode and the reaction region of the reference electrode are added with the ruthenium compound as an electron mediator, $R^2<0.98$, CVs of the four parallel measurements are less than 7.5%, but the potential differences measured for different urea concentrations have a poor gradient (the slope of the linear equation is 0.3029), and the samples with different concentrations (especially low-concentration samples) cannot be effectively distinguished, so it is prone to measurement errors when low-concentration samples are tested.

TABLE 3

| Test Result | Hematocrit (HCT) 42% Urea concentration (mM) | | | |
|---|---|---|---|---|
| | 4.5 | 14.5 | 24.5 | 41.5 |
| | Potential difference ΔE (mV) | | | |
| Rep. 1 | 9.9 | 13.0 | 18.0 | 20.0 |
| Rep. 2 | 10.0 | 13.2 | 17.4 | 21.7 |
| Rep. 3 | 9.0 | 14.6 | 16.9 | 20.8 |
| Rep. 4 | 10.1 | 12.9 | 17.3 | 21.1 |
| Average value | 9.74 | 13.41 | 17.38 | 20.90 |
| SD | 0.52 | 0.80 | 0.44 | 0.69 |
| CV | 5.3% | 6.0% | 2.5% | 3.3% |

Embodiment 3: Selection of Electron Mediator

The electron mediator in the reaction reagent 1 of the present invention is replaced with potassium ferricyanide or potassium ferrocyanide; when the electron mediator is replaced with potassium ferricyanide, the second reaction reagent on the indication electrode and the first reaction reagent on the reference electrode are as shown in the reaction reagent 2 of the present invention in Embodiment 1; and when the electron mediator is replaced with potassium ferrocyanide, the second reaction reagent on the indication electrode and the first reaction reagent on the reference electrode are as shown in the reaction reagent 3 of the present invention in Embodiment 1.

Four kinds of whole blood samples with different urea concentrations (5.4 mM, 17.5 mM, 25.4 mM and 31.8 mM) are selected and tested according to the potential difference test method in Embodiment 2. Each kind of whole blood sample with different urea concentration is tested multiple times (usually 3 to 5 times) in parallel, and then an average value of the potential differences obtained in multiple measurements is calculated. In view of the linear relationship between the urea concentration in the sample such as blood and the tested potential difference, a linear equation between the two can be obtained.

Figure 10:
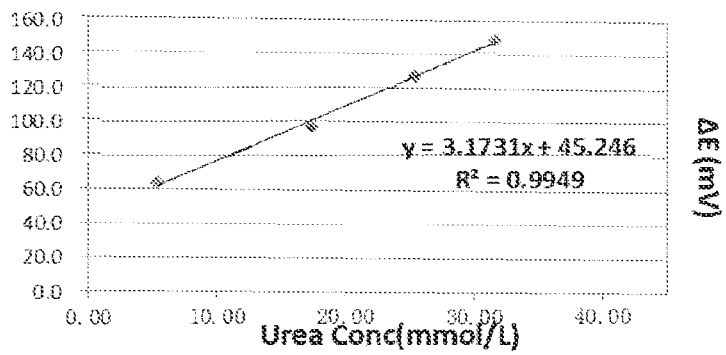
FIG. 10 is a diagram of test results obtained by a potentiometric method when a reaction reagent 2 of the present invention in Embodiment 1 is added to the reaction regions of the indication electrode and the reference electrode.

When the reaction regions of the indication electrode and the reference electrode are added with the reaction reagent 2 of the present invention in Embodiment 1, the test results are as shown in Table 4 and FIG. 10. It can be seen from Table 4 and FIG. 10 that, compared to the case where no electron mediator is added, the electrode system produces a significant electrical signal, which can be known from the measured average potential difference value >65 mV. In addition, $R^2>0.98$, but when the urea concentrations are respectively 17.5 mM, 25.4 mM and 31.8 mM, CVs of the five parallel measurements are all more than 10%, the highest is 17.6%, but all are less than 20%.

TABLE 4

| Test Result | Hematocrit (HCT) 42% Urea concentration (mM) | | | |
|---|---|---|---|---|
| | 5.4 | 17.5 | 25.4 | 31.8 |
| | Potential difference ΔE (mV) | | | |
| Rep. 1 | 63.1 | 103.6 | 112.4 | 136.8 |
| Rep. 2 | 64.5 | 105.1 | 128.4 | 151.6 |
| Rep. 3 | 70.1 | 94.1 | 136.7 | 181.6 |
| Rep. 4 | 62.2 | 78.2 | 146.4 | 111.2 |
| Rep. 5 | 65.2 | 93.9 | 98.5 | 155.3 |
| Average value | 65.02 | 94.98 | 124.47 | 147.28 |
| SD | 3.06 | 10.75 | 19.15 | 25.85 |
| CV | 4.7% | 11.3% | 15.4% | 17.6% |

Figure 11:
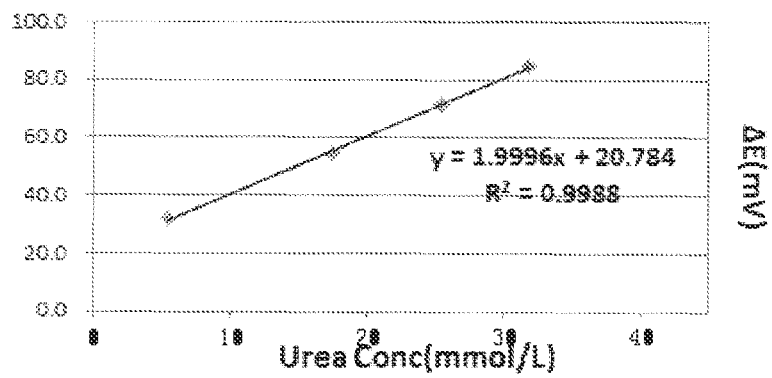
FIG. 11 is a diagram of test results obtained by a potentiometric method when a reaction reagent 3 of the present invention in Embodiment 1 is added to the reaction regions of the indication electrode and the reference electrode.

When the reaction regions of the indication electrode and the reference electrode are added with the reaction reagent 3 of the present invention in Embodiment 1, the test results are as shown in Table 5 and FIG. 11. It can be seen from Table 5 and FIG. 11 that, compared to the case where no electron mediator is added, the electrode system produces a significant electrical signal, which can be known from the measured average potential difference value >32 mV. In addition, $R^2>0.98$, but when the urea concentrations are respectively 5.4 mM and 17.5 mM, CVs of the five parallel measurements are all more than 10%, the highest is 19.7%, but all are less than 20%.

TABLE 5

| Test Result | Hematocrit (HCT) 42% Urea concentration (mM) | | | |
|---|---|---|---|---|
| | 5.4 | 17.5 | 25.4 | 31.8 |
| | Potential difference ΔE (mV) | | | |
| Rep. 1 | 33.2 | 61.8 | 73.3 | 82.7 |
| Rep. 2 | 30.8 | 63.1 | 69.9 | 88.7 |
| Rep. 3 | 22.0 | 45.8 | 69.9 | 78.7 |
| Rep. 4 | 36.1 | 50.9 | 67.5 | 86.6 |
| Rep. 5 | 38.4 | 51.7 | 73.3 | 87.0 |
| Average value | 32.10 | 54.65 | 71.83 | 84.74 |
| SD | 6.33 | 7.47 | 4.33 | 4.03 |
| CV | 19.7% | 13.7% | 6.0% | 4.8% |

Embodiment 4: Evaluation of Different Electrochemical Methods

The whole blood samples with different urea concentrations are tested by means of the reaction reagent 1, the reaction reagent 2 and the reaction reagent 3 of the present invention in Embodiment 1 according to the conventional current test method (that is, the potentiometric biosensor in FIG. 1 or 2 of the present invention is connected to a test device, specifically an electrochemical workstation Biologic VSP EC-Lab, and the test device applies a 0.4V voltage between the indication electrode and the reference electrode; after a sample is added, the second reaction region on the indication electrode and the first reaction region on the reference electrode undergo an enzymatic reaction and electrons are generated, the resulting current is tested, and finally, the urea concentration in the whole blood sample is calculated from the measured current value). In order to facilitate comparison, potentiometric test is also performed according to the method in Embodiment 2.

Figure 12:
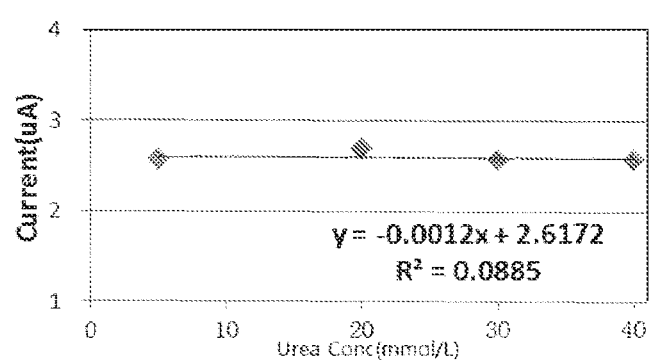
FIG. 12 is a diagram of test results obtained by a current method when the reaction reagent 1 of the present invention in Embodiment 1 is added to the reaction regions of the indication electrode and the reference electrode.

When the reaction regions of the indication electrode and the reference electrode are added with the reaction reagent 1 of the present invention in Embodiment 1, the test results of the current test method are as shown in Table 6 and FIG. 12. It can be seen from Table 6 and FIG. 12 that the current values measured for the whole blood samples with different urea concentrations have poor gradients, the whole blood samples with different concentrations cannot be effectively distinguished, and therefore it is prone to measurement errors.

TABLE 6

| Test Result | Hematocrit (HCT) 42% Urea concentration (mM) | | | |
|---|---|---|---|---|
| | 4.5 | 14.5 | 24.5 | 41.5 |
| | Current (μA) | | | |
| Rep. 1 | 2.50 | 2.63 | 2.64 | 2.69 |
| Rep. 2 | 2.78 | 2.87 | 2.35 | 2.40 |
| Rep. 3 | 2.43 | 2.54 | 2.68 | 2.56 |
| Average value | 2.57 | 2.68 | 2.56 | 2.55 |
| SD | 0.19 | 0.17 | 0.18 | 0.15 |
| CV | 7.4% | 6.3% | 7.0% | 5.9% |

Figure 13:
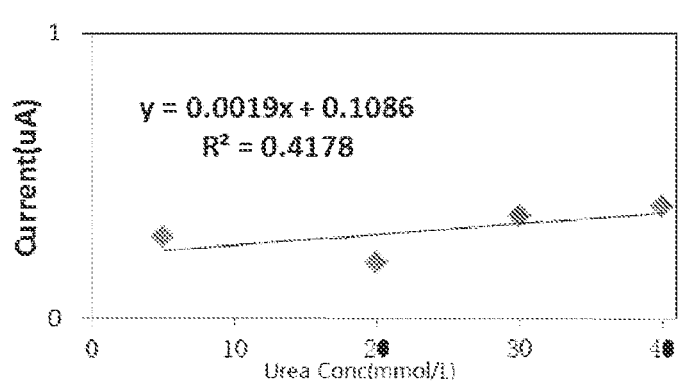
FIG. 13 is a diagram of test results obtained by a current method when the reaction reagent 2 of the present invention in Embodiment 1 is added to the reaction regions of the indication electrode and the reference electrode.

When the reaction regions of the indication electrode and the reference electrode are added with the reaction reagent 2 of the present invention in Embodiment 1, the test results of the current test method are as shown in Table 7 and FIG. 13. It can be seen from Table 7 and FIG. 13 that the current values measured for the samples with different urea concentrations have poor gradients, the samples with different concentrations cannot be effectively distinguished, and therefore it is prone to measurement errors.

TABLE 7

| Test Result | Hematocrit (HCT) 42% Urea concentration (mM) | | | |
|---|---|---|---|---|
| | 4.5 | 14.5 | 24.5 | 41.5 |
| | Current (μA) | | | |
| Rep. 1 | 0.13 | 0.00 | 0.21 | 0.20 |
| Rep. 2 | 0.13 | 0.16 | 0.16 | 0.20 |
| Rep. 3 | 0.17 | 0.14 | 0.17 | 0.19 |
| Average value | 0.14 | 0.10 | 0.18 | 0.20 |
| SD | 0.02 | 0.09 | 0.03 | 0.0047 |
| CV | 14.3% | 90.0% | 16.7% | 2.4% |

Figure 14:
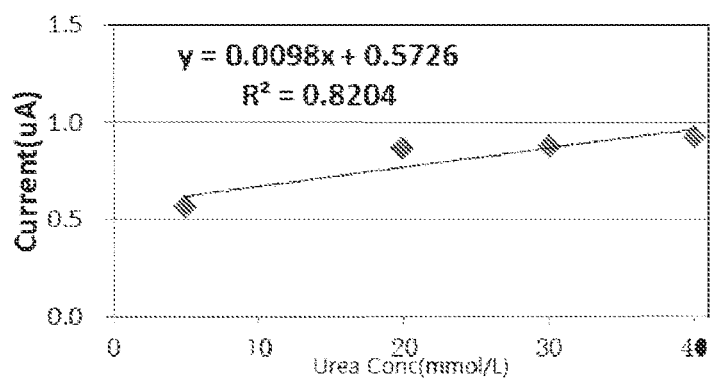
FIG. 14 is a diagram of test results obtained by a current method when the reaction reagent 3 of the present invention in Embodiment 1 is added to the reaction regions of the indication electrode and the reference electrode.

When the reaction regions of the indication electrode and the reference electrode are added with the reaction reagent 3 of the present invention in Embodiment 1, the test results of the current test method are as shown in Table 8 and FIG. 14. It can be seen from Table 8 and FIG. 14 that the current values measured for the whole blood samples with different urea concentrations have poor gradients, the whole blood samples with different urea concentrations cannot be effectively distinguished, and therefore it is prone to measurement errors.

TABLE 8

| Test Result | Hematocrit (HCT) 42% Urea concentration (mM) | | | |
|---|---|---|---|---|
| | 4.5 | 14.5 | 24.5 | 41.5 |
| | Current (μA) | | | |
| Rep. 1 | 0.59 | 0.87 | 0.85 | 0.92 |
| Rep. 2 | 0.54 | 0.90 | 0.86 | 0.92 |
| Rep. 3 | 0.56 | 0.82 | 0.89 | 0.92 |
| Average value | 0.57 | 0.86 | 0.87 | 0.92 |
| SD | 0.03 | 0.04 | 0.02 | 0.00 |
| CV | 5.3% | 4.7% | 2.3% | 0 |

Embodiment 5: Assessment on the Influence of Hematocrit (HCT)

In the electrochemical detection on a component such as glucose in the sample, the hematocrit affects the test results. To this end, the present invention assesses the influence of different hematocrits on the test results of the potentiometric method. A whole blood sample with low urea concentration (4.5 mM) and a whole blood sample with high urea concentration (43.5 mM) are selected to test potential differences under different hematocrits. The test results are shown in Table 9.

TABLE 9

| Test Result | Hematocrit (HCT) | | | | | |
|---|---|---|---|---|---|---|
| | 30% | 42% | 60% | 30% | 42% | 60% |
| | Urea concentration (mM) | | | | | |
| | 4.5 | | | 43.5 | | |
| | Potential difference ΔE (mV) | | | | | |
| Rep. 1 | 33.9 | 39.5 | 35.7 | 91.6 | 86.6 | 80.0 |
| Rep. 2 | 40.5 | 37.1 | 36.4 | 90.9 | 85.1 | 78.2 |

TABLE 9-continued

| | Hematocrit (HCT) | | | | | |
|---|---|---|---|---|---|---|
| | 30% | 42% | 60% | 30% | 42% | 60% |
| | Urea concentration (mM) | | | | | |
| | 4.5 | | | 43.5 | | |
| Test Result | Potential difference ΔE (mV) | | | | | |
| Rep. 3 | 39.6 | 35.1 | 36.6 | 90.0 | 86.4 | 81.4 |
| Rep. 4 | 38.4 | 35.3 | 37.0 | 95.0 | 83.8 | 76.4 |
| Average value | 38.09 | 36.77 | 36.41 | 91.88 | 85.49 | 79.02 |
| SD | 2.93 | 2.02 | 0.56 | 2.20 | 1.30 | 2.14 |
| CV | 7.7% | 5.5% | 1.5% | 2.4% | 1.5% | 2.7% |
| Deviation (average value − control value) | 1.3 | — | −0.4 | 6.4 | — | −6.5 |
| Deviation/control value | 3.5% | — | −1.1% | 7.5% | — | −7.6% |

Taking the average value of the potential differences tested at HCT of 42% as a control value, it can be seen that the average value of the potential differences detected when HCT=30% and when HCT=60% is different from the average value of the potential differences detected when HCT=42% within 10%. It can be seen that HCT has comparatively little interference to the test results.

The invention claimed is:

1. A method for testing the urea concentration in a sample, comprising the following steps:
   (1) providing an open-circuit potentiometric biosensor;
   (2) inserting the open-circuit potentiometric biosensor into a test instrument;
   (3) adding the sample to the open-circuit potentiometric biosensor, and allowing the sample to chemically react with the first reaction reagent and the second reaction reagent; and
   (4) testing the potential difference between the first electrode and the second electrode by means of the test instrument using an open-circuit potentiometric method, and determining the urea concentration in the sample based on the potential difference measured in the open-circuit potentiometric method,
   wherein
   the open-circuit potentiometric biosensor comprises a sample addition end, an electrical connection end, an insulating substrate, an electrode system comprising a reference electrode and an indication electrode, a conductive layer, a reaction region forming layer, a channel forming layer and an upper cover layer;
   the conductive layer is disposed on the insulating substrate, and comprises a first contact and a second contact that are located at the electrical connection end, an indication electrode and a reference electrode that are located at the sample addition end, a first conductive trace for connecting the reference electrode with the first contact, and a second conductive trace for connecting the indication electrode with the second contact;
   the reaction region forming layer covers the electrode system and is provided with a first reaction hole and a second reaction hole that are spaced apart, the first reaction hole exposes at least a part of the reference electrode and forms a first reaction region on the reference electrode, and the second reaction hole exposes at least a part of the indication electrode and forms a second reaction region on the indication electrode;
   the channel forming layer is disposed on the reaction region forming layer, provided with an opening in the sample addition end, and the opening simultaneously exposes at least a part of the first reaction region and at least a part of the second reaction region;
   the upper cover layer is disposed on the channel forming layer and provided with a vent, the upper cover layer forms a sample channel together with the opening, the reaction region forming layer and the insulating substrate, the vent is located above the sample channel, a sample addition port is provided in the sample addition end, and a sample enters the sample channel through the sample addition port; and
   a first reaction reagent is located on the first reaction region and contains an electron mediator but does not contain urease, and a second reaction reagent is located on the second reaction region and contains urease but does not contain an electron mediator.

2. The method according to claim 1, wherein the electron mediator has a concentration of 1.0-4.5% (w/w).

3. The method according to claim 1, wherein the electron mediator is selected from a ruthenium compound, potassium ferricyanide or potassium ferrocyanide, the ruthenium compound has a chemical structural formula $[Ru(NH_3)_5X]^{n+}$, X is selected from $NH_3$, halogen ions, CN, pyridine or nicotinamide, and n is 2 or 3.

4. The method according to claim 3, wherein the compound is $[Ru(NH_3)_6]Cl_3$.

5. The method according to claim 1, wherein the width of the opening of the channel forming layer is 1.0 to 2.5 mm, and the widths of the second reaction region and the first reaction region are approximately 2 to 3 times the width of the opening.

6. The method according to claim 1, wherein the first reaction reagent and the second reaction reagent further contain a polymer binder, a surfactant, a buffer, and a stabilizer; the polymer binder is a cellulose derivative, and has a concentration of 0.01-10% (W/W); the surfactant is selected from a PEG series surfactant, a Tween series surfactant, sodium cholate, CHAP, Triton X-100 or hexadecyl choline, and has a concentration of 0.01% to 5% (w/w); the buffer is selected from citric acid buffer, phosphate buffer or Tris-HCl buffer; and the stabilizer is selected from a sugar, a sugar alcohol, an amino acid, a protein or a carboxyl containing organic acid, and has a concentration of 0.1% to 50%.

7. The method according to claim 1, wherein the urease has a concentration of 2280 to 8712 U/mL.

8. The method according to claim 1, wherein the urea concentration is determined from a direct linear relationship between the tested potential difference and the urea concentration in the sample.

* * * * *